United States Patent [19]

Le Fur et al.

[11] 4,416,888
[45] Nov. 22, 1983

[54] 3-(2-(4-PIPERIDYL)-1-ALKYL-ETHYL)-INDOLES AND THEIR USE AS MEDICAMENTS

[75] Inventors: Gerard R. Le Fur, Plessis Robinson; Francois Audiau, Charenton, both of France

[73] Assignee: Pharmindustrie, Gennevilliers, France

[21] Appl. No.: 374,365

[22] Filed: May 3, 1982

[30] Foreign Application Priority Data

May 22, 1981 [FR] France .......... 8110220

[51] Int. Cl.³ .................. A61K 31/395; C07D 101/06
[52] U.S. Cl. ..................................... 424/267; 546/201
[58] Field of Search ......................... 546/201; 424/267

[56] References Cited

U.S. PATENT DOCUMENTS 3,136,770  6/1964  Gray ..................................... 546/201

FOREIGN PATENT DOCUMENTS

| 7258 | 1/1980 | European Pat. Off. | 546/201 |
| 1289690 | 2/1962 | France | 546/201 |
| 1693M | 2/1963 | France | 546/201 |
| 1510003 | 12/1967 | France | 546/201 |
| 6291M | 9/1968 | France | 546/201 |
| 925429 | 5/1963 | United Kingdom | 546/201 |
| 1023781 | 3/1966 | United Kingdom | 546/201 |

OTHER PUBLICATIONS

Gray et al. "J. Org. Chem.", vol. 26, pp. 3368-3372 (1961).

Primary Examiner—Robert T. Bond
Attorney, Agent, or Firm—Beveridge, DeGrandi & Kline

[57] ABSTRACT

Compounds of the general formula;

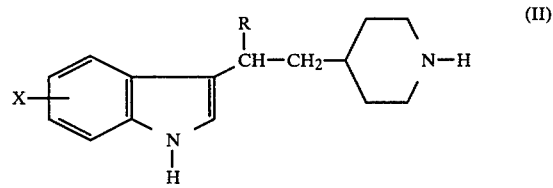

wherein R represents an alkyl group having 1 to 3 carbon atoms and X represents a hydrogen or halogen atom are disclosed together with methods for their preparation and their use in the treatment of migraines, as anti-thrombosis agents or as rapid acting thymoanaleptic medicaments.

4 Claims, No Drawings

3-(2-(4-PIPERIDYL)-1-ALKYL-ETHYL)-INDOLES AND THEIR USE AS MEDICAMENTS

The present invention relates to new indole derivatives and their use as medicaments.

French Pat. No. 75.38051 (No. 2,334,358) filed on Dec. 12, 1975 and corresponding to U.S. Pat. No. 4,064,255, describes indole derivatives which are active as specific inhibitors of serotonin uptake by neurons, and which may thus be used as psychotropic medicaments, especially anti-depressants. As such, special reference may be made to 3-[2-(4-piperidyl)-ethyl]-indole of the formula:

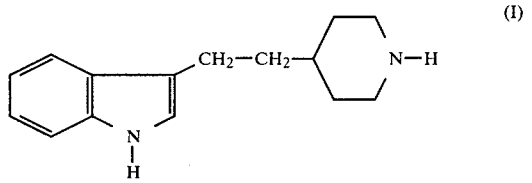

(I)

or indalpine, G. Le Fur and coll. Life Sciences 23, 1959 (1978).

The object of the present invention with respect to new products is compounds of the general formula:

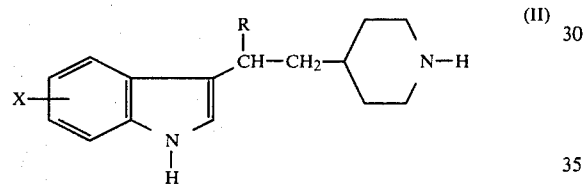

(II)

wherein R represents an alkyl group containing 1 to 3 carbon atoms and X represents a hydrogen or halogen atom, for example fluorine or chlorine.

It has been found that the compounds of formula (II) possess not only the ability, like indalpine, to inhibit serotonin uptake but also the property of inducing the release of the serotonin which is either contained in the neurons or in the blood platelets.

This dual function manifests itself in a more intense and more rapid action on depression owing to the neuron release of serotonin in the synaptic cleft, together with inhibition of uptake. The release of serotonin from the platelets into the blood plasma leads to an improvement in migraine condititons; in addition, the depletion of the platelets in serotonin prevents arterial thrombi from forming.

Compounds of the general formula (II) may be prepared by action on compounds of the general formula:

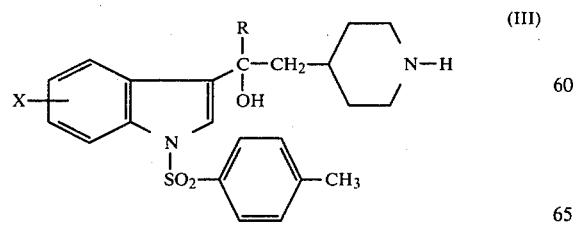

(III)

wherein R and X have the same significance as in formula (II), of a metallic hydride such as aluminum lithium hydride in an ether, such as diethyl ether or tetrahydrofuran, or in a mixture of an ether and a hydrocarbon such as toluene, at a temperature ranging from 0° C. to the boiling point of the solvent used. Other metallic hydrides which may be used include lithium trimethoxyaluminium hydride, other hydrocarbons include benzene and xylene, and other ethers include dioxane, dimethoxyethane, and diglyme.

The starting materials of formula (III) may be prepared according to the following reaction scheme:

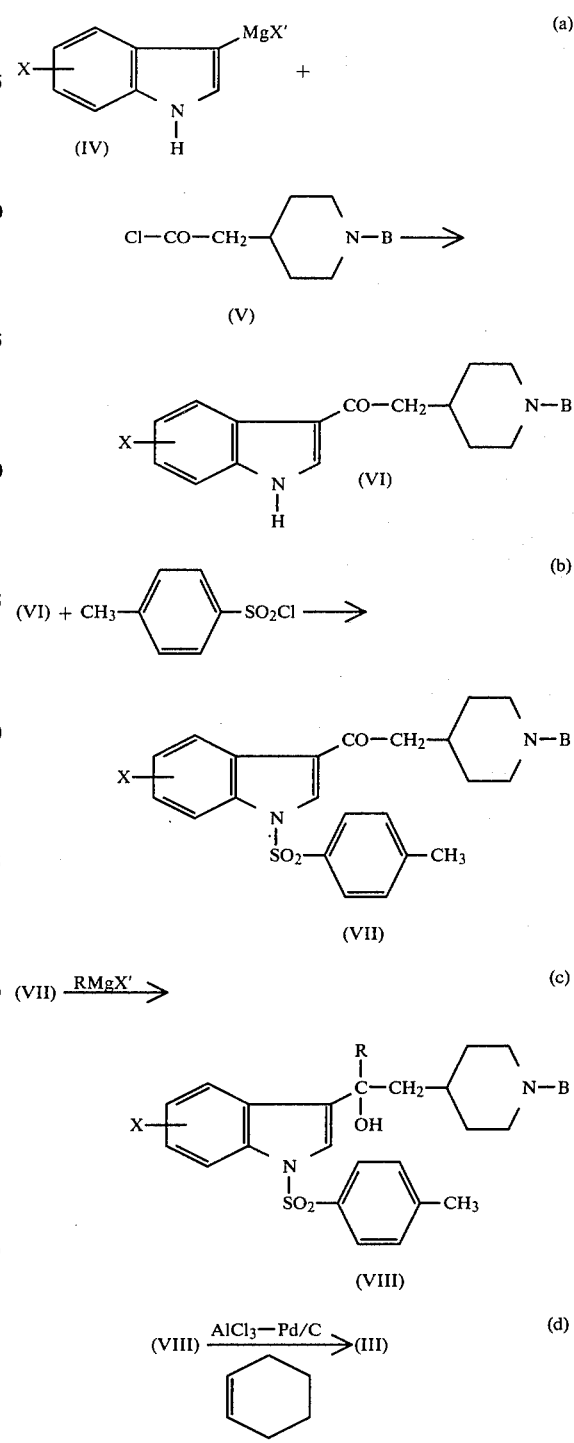

(a) To the Grignard reagent of formula (IV) in which X has the same significance as formula (II) and X' represents a chlorine, bromine or iodine atom (obtained by the action on the corresponding indole, of a magnesium-alkyl halide such as magnesium methyl chloride, bromide or iodide in an ether such as diethyl ether) is added at a temperature ranging from −10° C. to +20° C. the acid chloride of formula (V) (wherein B represents the benzyloxycarbonyl group) in solution in an ether, such as tetrahydrofuran or in a hydrocarbon such as toluene.

(b) The ketone of formula (VI) thus obtained is tosylated by the action of tosyl chloride at a temperature ranging from −20° C. to +20° C. in an inert solvent and in the presence of a base. One can for example, operate with pyridine which has the dual function of being a solvent and a base, or with acetone in the presence of potassium carbonate.

In the following stage (c) the Grignard reagent of the formula RMgX' wherein R has the same significance as in formula (II) and wherein X' represents a chlorine, bromine or iodine atom, is reacted with the product of formula (VII) thus obtained, in an inert solvent such as diethyl ether or tetrahydrofuran at a temperature ranging from 0° to 30° C. The hydrolysis of the reaction mixture must be effected at a low temperature (between 0° and 10° C.) and at a pH between 5 and 7.

Stage (d) consists in the cleavage of the protective group B under conditions preventing dehydration of the alcohol function of the chain. Cyclohexene is advantageously used for this purpose in the presence of aluminum chloride and palladized carbon, at the boiling point of cyclohexene.

The piperidine derivative of formula (V) may be prepared in 2 stages from 4-piperidyl acetic acid according to I. De Graw, J. Hetero. Chem., 3, 90 (1966).

The reaction mixtures obtained according to the various procedures described above are treated according to conventional methods either physical (evaporation, extraction by using a solvent, distillation, crystallization, chromatography etc.) or chemical (salt formation and regeneration of the base etc.) so as to isolate the compounds of formula (II) in the pure state.

The compounds of formula (II) in the form of the free base, may, if desired, be converted into addition salts with a pharmaceutically acceptable mineral or organic acid, e.g. hydrochloric acid, sulfuric acid, maleic acid or citric acid, by the action of such an acid in a suitable solvent, e.g. ethanol, acetone or ethyl acetate.

The following example illustrates the invention without limiting it.

EXAMPLE

3-[2-(4-Piperidyl)-1-Methyl-Ethyl]-Indole

A suspension of 16 g lithium aluminum hydride, 10 g of 1-(4-piperidyl)-2-(1-p-toluenesulfonyloxy-3-indolyl)-2-propanol in 300 ml ether and 300 ml toluene was heated for 5 hours at a temperature of 50° C.

Following hydrolysis, the organic phase was washed with water and evaporated under vacuum. 4.8 g of an oil were obtained, which was purified by chromatography over silica gel (eluant: toluene-ethanol-diethylamine: 10-10-1). After crystallization in 6 ml of acetonitrile, 1.9 g of 3-[2-(4-piperidyl)-1-methyl-ethyl]-indole which melted at 125° C. were obtained.

The starting product was prepared in the following way:

17.6 g of indole in solution in 100 ml of ether were added to a magnesium methyl iodide solution prepared from 6.5 g magnesium and 38.6 g methyl iodide in 150 ml ethyl ether. Heating under reflux took place for 2 hours and the solution was cooled to 0° C. before adding, drop by drop while stirring, a solution of 36.3 g of 1-benzyloxycarbonyl-4-piperidyl-acetyl chloride (U.S. Pat. No. 4,064,255) in 300 ml toluene. The solution was stirred for 2 hours at 10° C. and then hydrolyzed with 170 ml of 2 N hydrochloric acid. 25.8 g of 2-(1-benzyloxycarbonyl-4-piperidyl)-1-(3-indolyl)-ethanone melting at 122° C. were obtained and then converted into a tosylated derivative by the action of 15.7 g of tosyl chloride in the presence of 27.8 g potassium carbonate in 400 ml of acetone. 34.5 g of 2-(1-benzyloxycarbonyl-4-piperidyl)-1-(1-p-toluenesulfonyloxy-3-indolyl)-ethanone were obtained and put into suspension in 600 ml ethyl ether. This suspension was added, little by little, to a magnesium methyl iodide solution prepared from 3.1 g of magnesium and 18.5 g of methyl iodide in 200 ml of ethyl ether. The mixture was stirred over night at the ambient temperature and hydrolyzed at about 5° C. with 650 ml of a 20% by weight aqueous solution of ammonium acetate. 35.5 g of 1-(1-benzyloxycarbonyl-4-piperidyl)-2-(1-tosyl-3-indolyl)-2-propanol were obtained. The piperidine protective group was then eliminated by the action of cyclohexene in the presence of aluminum chloride and 10% palladized carbon; the reagents were added at or near 0° C. in an inert atmosphere. The process was completed by heating under reflux for 4 hours. After filtration, concentration under vacuum and purification by silica gel chromatography (eluant: toluene-ethanol-diethylamine = 5-5-1), 10 g of 1-(4-piperidyl)-2-(1-p-toluenesulfonyloxy-3-indolyl)-2-propanol were obtained which were used as such for the preparation of 3-[2-(4-piperidyl)-1-methyl-ethyl]-indole.

PHARMACOLOGICAL PROPERTIES

It is known that serotonin uptake by the blood platelets is a good model for the uptake of this amine by the neurons (cf. J. Tuomisto, J. Pharm., Pharmac., 26, 92 (1974). When applied to the study of medicaments, any method involving the use of blood platelets is of great interest because it allows the use of human cells, so that its estimation character is good.

The capacity of products inhibiting serotonin uptake or which induce serotonin release was shown on human blood platelets, by J. L. David and Coll. "Platelets Function and Thrombosis, a Review of Methods" p. 335 (Plenum Press, London, 1972).

1. Inhibition of Serotonin Uptake

The results are expressed by inhibitory dose 50% or $I_{50}$ which represents the dose of the product in micromoles per liter which reduce the rate of serotonin uptake by 50%.

2. Serotonin Release

The action of the products on serotonin release is tested at a concentration of $5 \times 10^{-5}$ moles per liter. The results obtained are expressed as a percentage of increased serotonin release in relation to the results obtained with the controls.

The results obtained with the compounds according to the invention are compiled in the table below. This table shows, by way of comparison, the results obtained with two reference products (imipramine and p-chloroamphetamine) and with indalpine.

TABLE

| Product | Inhibition of serotonin uptake I$_{50}$ (micromoles per liter) | Percent of increased serotonin release (product concentration: $5 \times 10^{-5}$ moles per liter) |
| --- | --- | --- |
| Example 1 | 0.05 | 62 |
| Indalpine | 0.035 | 22 |
| Imipramine | 0.4 | 12 |
| p-chloroamphetamine | 12 | 51 |

The products of the invention are therefore not only powerful inhibitors of serotonin uptake (activity equivalent to that of indalpine), but are, moreover, powerful agents of serotonin release, which are even more active than p-chloroamphetamine.

The interesting feature of these compounds lies in the fact that like parachloroamphetamine, they induce serotonin release without presenting any of the pharmacological properties which characterize amphetamines (anorexia, hypermotility).

TOXICOLOGICAL PROPERTIES

The acute toxicity of the products has been established in male mice CD$_1$ (Charles RIVER) by oral administration. The compounds according to the invention are relatively not very toxic substances. For example, the product of Example 1 is non-toxic in the mouse if administered at a dose of 100 mg/kg.

THERAPEUTIC APPLICATION

The compounds of the invention and their pharmaceutically acceptable salts may be used in human therapy in the form of tablets, capsules, gelatine coated pills, suppositories, ingestible or injectable solutions etc., as regulators of the serotonin-dependent vascular tonus, especially in the treatment of migraines, as anti-thrombosis agents and as thymoanaleptic medicaments with a particularly rapid action (on account of their action on the release of serotonin).

For the foregoing purposes the compounds described above may be administered in a therapeutically effective amount, such as to a mammal; orally or parenterally.

For purposes of injection the compounds described above can be prepared in the form of solutions, suspensions or emulsions in vehicles conventionally employed for this purpose.

The posology depends on the effects required and on the method of administration used. For example, by oral administration, it may be between 15 and 250 mg of active substance per day, with unit doses of between 5 and 50 mg.

Appropriate pharmaceutically acceptable carriers, diluents and adjuvants may be used together with the compounds described herein in order to prepare the desired compositions for use in treatment of mammals according to the invention.

The pharmaceutical compositions of this invention will contain the active compound together with a solid or liquid pharmaceutically acceptable nontoxic carrier. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. Such compositions will contain an effective therapeutic amount of the active compound together with a suitable amount of carrier so as to provide the form for proper administration to the host.

What is claimed is:

1. A process for the preparation of a compound of the formula:

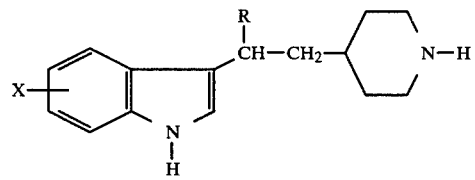

wherein R represents alkyl having 1 to 3 carbon atoms and X represents hydrogen or halogen which comprises reacting a compound of the formula:

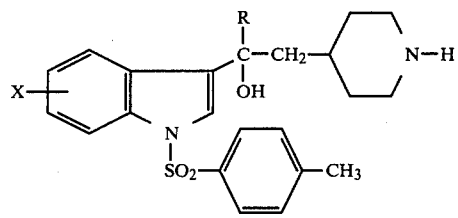

with a metallic hydride in an ester or a mixture of an ether and a hydrocarbon, at a temperature between 0° C. and the boiling point of the solvent.

2. A medicament useful as an agent for inhibiting serotonin uptake and for serotonin release comprising an effective amount of a compound of the formula:

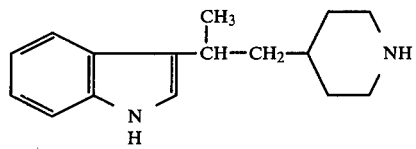

or its salt with a pharmaceutically acceptable acid together with a pharmaceutically effective carrier.

3. A medicament as claimed in claim 2 for use in the treatment of migraine, as anti-thrombosis agent or as thymoanaleptic agent.

4. A method of treating a mammal afflicted with depression or migraine conditions or to prevent the formation of arterial thrombi which comprises administering to said mammal a therapeutically effective amount of a composition containing a compound of the formula:

7
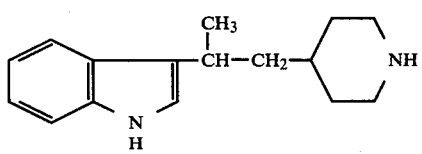
or a pharmaceutically acceptable salt thereof in a pharmaceutically acceptable carrier therefor.
* * * * *
8
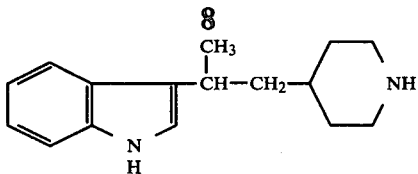
or a pharmaceutically acceptable salt thereof in a pharmaceutically acceptable carrier therefor.
* * * * *